US012749244B2

(12) United States Patent
Freiman et al.

(10) Patent No.: US 12,749,244 B2
(45) Date of Patent: Sep. 29, 2026

(54) PHYSICALLY-PRIMED DEEP-NEURAL-NETWORKS FOR GENERALIZED UNDERSAMPLED MRI RECONSTRUCTION

(71) Applicant: Technion Research & Development Foundation Limited, Haifa (IL)

(72) Inventors: Mordechay Pinchas Freiman, Zichron Yaakov (IL); Nitzan Avidan, Rosh Haayin (IL)

(73) Assignee: Technion Research & Development Foundation Limited, Haifa (IL)

( * ) Notice: Subject to any disclaimer, the term of this patent is extended or adjusted under 35 U.S.C. 154(b) by 488 days.

(21) Appl. No.: 18/449,681

(22) Filed: Aug. 14, 2023

(65) Prior Publication Data

US 2024/0054699 A1 Feb. 15, 2024

Related U.S. Application Data

(60) Provisional application No. 63/371,398, filed on Aug. 14, 2022.

(51) Int. Cl.

*G06T 12/20* (2026.01)
*A61B 5/00* (2006.01)
*A61B 5/055* (2006.01)

(52) U.S. Cl.

CPC .............. *G06T 12/20* (2026.01); *A61B 5/055* (2013.01); *A61B 5/7267* (2013.01)

(58) Field of Classification Search

None
See application file for complete search history.

(56) References Cited

U.S. PATENT DOCUMENTS

| | | | | |
|---|---|---|---|---|
| 2021/0217213 | A1* | 7/2021 | Cole | G01R 33/5608 |
| 2022/0101997 | A1* | 3/2022 | Iqbal | G06N 3/096 |
| 2023/0367850 | A1* | 11/2023 | Chen | G06F 18/214 |
| 2023/0408614 | A1* | 12/2023 | Speidel | G01R 33/4818 |
| 2024/0290487 | A1* | 8/2024 | Mosadegh | G16H 30/40 |
| 2025/0005888 | A1* | 1/2025 | Zhang | G06T 5/10 |
| 2025/0110196 | A1* | 4/2025 | Srivastava | G01R 33/5659 |

OTHER PUBLICATIONS

Xuan et al. (Multi-Modal MRI Reconstruction Assisted with Spatial Alignment Network), arXiv:2108.05603 [Submitted on Aug. 12, 2021 (v1), last revised Apr. 2, 2022 (this version, v3)], p. 4, left column, 2nd paragraph (Year: 2022).*

(Continued)

*Primary Examiner* — Miya J Cato
(74) *Attorney, Agent, or Firm* — Reches Patents

(57) ABSTRACT

A method for reconstructing spatial information, the method includes: (i) Obtaining an under-sampled frequency domain representation (FDR) of the spatial information. The under-sampled FDR was obtained by sampling an FDR of the spatial information with a sampling mask. (ii) Feeding the under-sampled FDR and the sampling mask to a machine learning process. (iii) Reconstructing the spatial information by the machine learning process. The machine learning process was trained using a training data set that includes training under-sampled FRDs of training spatial information, and one or more training sampling masks that were used to sample FDRs of training spatial information.

20 Claims, 7 Drawing Sheets

600

(56) References Cited

OTHER PUBLICATIONS

Ahmad, R., Bouman, C.A., Buzzard, G.T., Chan, S., Liu, S., Reehorst, E.T., Schniter, P., 2020. Plugand-play methods for magnetic resonance imaging: Using denoisers for image recovery. IEEE signal processing magazine 37, 105-116.
Akc,akaya, M., Moeller, S., Weingartner, S., Ugurbil, K., 2019. Scan-specific robust artificial-neuralnetworks for k-space interpolation (raki) reconstruction: Database-free deep learning for fast imaging. Magnetic resonance in medicine 81, 439-453.
Cheng, J.Y., Mardani, M., Alley, M.T., Pauly, J.M., Vasanawala, S.S., 2018. Deepspirit: generalized parallel imaging using deep convolutional neural networks, in: Annual Meeting of the International Society of Magnetic Resonance in Medicine.
Cui, Z.X., Jia, S., Zhu, Q., Liu, C., Qiu, Z., Liu, Y., Cheng, J., Wang, H., Zhu, Y., Liang, D., 2022. K-unn: k-space interpolation with untrained neural network. URL: https://arxiv.org/abs/2208.05827, doi:10.48550/ARXIV.2208.05827.
Geng, C., Jiang, M., Fang, X., Li, Y., Jin, G., Chen, A., Liu, F., 2023. Hfist-net: High-throughput fast iterative shrinkage thresholding network for accelerating mr image reconstruction. Computer Methods and Programs in Biomedicine 232, 107440.
Hong, G.Q., Wei, Y.T., Morley, W.A., Wan, M., Mertens, A.J., Su, Y., Cheng, H.L.M., 2023. Dual-domain accelerated mri reconstruction using transformers with learning-based undersampling. Computerized Medical Imaging and Graphics 106, 102206.
Liang, D., Cheng, J., Ke, Z., Ying, L., 2019. Deep mri reconstruction: unrolled optimization algorithms meet neural networks. arXiv preprint arXiv:1907.11711 .
Lustig, M., Pauly, J.M., 2010. Spirit: iterative self-consistent parallel imaging reconstruction from arbitrary k-space. Magnetic resonance in medicine 64, 457-471.
Lv, J., Li, G., Tong, X., Chen, W., Huang, J., Wang, C., Yang, G., 2021. Transfer learning enhanced generative adversarial networks for multi-channel mri reconstruction. Computers in Biology and Medicine 134, 104504.
Pawar, K., Egan, G.F., Chen, Z., 2021. Domain knowledge augmentation of parallel mr image reconstruction using deep learning. Computerized Medical Imaging and Graphics 92, 101968.
Quan, T.M., Nguyen-Duc, T., Jeong, W.K., 2018. Compressed sensing mri reconstruction using a generative adversarial network with a cyclic loss. IEEE transactions on medical imaging 37, 1488-1497.
Shaul, R., David, I., Shitrit, O., Raviv, T.R., 2020. Subsampled brain mri reconstruction by generative adversarial neural networks. Medical Image Analysis 65, 101747.
Wang, W., Shen, H., Chen, J., Xing, F., 2023. Mhan: Multi-stage hybrid attention network for mri reconstruction and super-resolution. Computers in Biology and Medicine , 107181.
Wu, Z., Liao, W., Yan, C., Zhao, M., Liu, G., Ma, N., Li, X., 2023. Deep learning based mri reconstruction with transformer. Computer Methods and Programs in Biomedicine 233, 107452.
Yazdanpanah, A.P., Afacan, O., Warfield, S., 2019. Deep plug-and-play prior for parallel mri reconstruction, in: 2019 IEEE/CVF International Conference on Computer Vision Workshop (ICCVW), IEEE. pp. 3952-3958.
Zach, M., Knoll, F., Pock, T., 2022. Stable deep mri reconstruction using generative priors. URL: https://arxiv.org/abs/2210.13834, doi: 10.48550/ARXIV.2210.13834.
Zhang, Y., Lyu, J., Bi, X., 2021. A dual-task dual-domain model for blind mri reconstruction. Computerized Medical Imaging and Graphics 89, 101862.
Zhao, X., Yang, T., Li, B., Zhang, X., 2023. Swingan: A dual-domain swin transformer-based generative adversarial network for mri reconstruction. Computers in Biology and Medicine 153, 106513.
Z.-P. Liang and P. C. Lauterbur, Principles of magnetic resonance imaging. SPIE Optical Engineering Press Bellingham, 2000.
J. Zbontar, F. Knoll, A. Sriram, T. Murrell, Z. Huang, M. J. Muckley, A. Defazio, R. Stern, P. Johnson, M. Bruno et al., "fastmri: An open dataset and benchmarks for accelerated mri," arXiv preprint arXiv:1811.08839, 2018.
D. A. Feinberg, J. D. Hale, J. C. Watts, L. Kaufman, and A. Mark, "Halving mr imaging time by conjugation: demonstration at 3.5 kg." Radiology, vol. 161, No. 2, pp. 527-531, 1986.
M. A. Griswold, P. M. Jakob, R. M. Heidemann, M. Nittka, V. Jellus, J. Wang, B. Kiefer, and A. Haase, "Generalized autocalibrating partially parallel acquisitions (grappa)," Magnetic Resonance in Medicine: An Official Journal of the International Society for Magnetic Resonance in Medicine, vol. 47, No. 6, pp. 1202-1210, 2002.
K. P. Pruessmann, M. Weiger, M. B. Scheidegger, and P. Boesiger, "Sense: sensitivity encoding for fast mri," Magnetic Resonance in Medicine: An Official Journal of the International Society for Magnetic Resonance in Medicine, vol. 42, No. 5, pp. 952-962, 1999.
K. Hammernik, T. Kustner, B. Yaman, Z. Huang, D. Rueckert, F. Knoll, and M. Akcakaya, "Physics-driven deep learning for computational magnetic resonance imaging," arXiv preprint arXiv:2203.12215, 2022.
M. Lustig, D. Donoho, and J. M. Pauly, "Sparse mri: The application of compressed sensing for rapid mr imaging," Magnetic Resonance in Medicine: An Official Journal of the International Society for Magnetic Resonance in Medicine, vol. 58, No. 6, pp. 1182-1195, 2007.
Y. Chen, C.-B. Schonlieb, P. Lio, T. Leiner, P. L. Dragotti, G. Wang, D. Rueckert, D. Firmin, and G. Yang, "Ai-based reconstruction for fast mri—a systematic review and meta-analysis," Proceedings of the IEEE, vol. 110, No. 2, pp. 224-245, 2022.
T. Eo, Y. Jun, T. Kim, J. Jang, H.-J. Lee, and D. Hwang, "Kiki-net: cross-domain convolutional neural networks for reconstructing undersampled magnetic resonance images," Magnetic resonance in medicine, vol. 80, No. 5, pp. 2188-2201, 2018.
A. Sriram, J. Zbontar, T. Murrell, A. Defazio, C. L. Zitnick, N. Yakubova, F. Knoll, and P. Johnson, "End-to-end variational networks for accelerated mri reconstruction," in International Conference on Medical Image Computing and Computer-Assisted Intervention. Springer, 2020, pp. 64-73.
V. Antun, F. Renna, C. Poon, B. Adcock, and A. C. Hansen, "On instabilities of deep learning in image reconstruction and the potential costs of ai," Proceedings of the National Academy of Sciences, vol. 117, No. 48, pp. 30 088-30 095, 2020.
A. Jalal, M. Arvinte, G. Daras, E. Price, A. G. Dimakis, and J. Tamir, "Robust compressed sensing mri with deep generative priors," Advances in Neural Information Processing Systems, vol. 34, pp. 14 938-14 954, 2021.
F. Liu, A. Samsonov, L. Chen, R. Kijowski, and L. Feng, "Santis: sampling-augmented neural network with incoherent structure for mr image reconstruction," Magnetic resonance in medicine, vol. 82, No. 5, pp. 1890-1904, 2019.
C. M. Hyun, H. P. Kim, S. M. Lee, S. Lee, and J. K. Seo, "Deep learning for undersampled mri reconstruction," Physics in Medicine & Biology, vol. 63, No. 13, p. 135007, 2018.
G. Yang, S. Yu, H. Dong, G. Slabaugh, P. L. Dragotti, X. Ye, F. Liu, S. Arridge, J. Keegan, Y. Guo et al., "Dagan: deep de-aliasing generative adversarial networks for fast compressed sensing mri reconstruction," IEEE transactions on medical imaging, vol. 37, No. 6, pp. 1310-1321, 2017.
S. Aja-Fernandez and G. Vegas-Sanchez-Ferrero, "Statistical analysis of noise in mri," Switzerland: Springer International Publishing, 2016.
J. C. Ye, "Compressed sensing mri: a review from signal processing perspective," BMC Biomedical Engineering, vol. 1, No. 1, pp. 1-17, 2019.
O. Ronneberger, p. Fischer, and T. Brox, "U-net: Convolutional networks for biomedical image segmentation," in International Conference on Medical image computing and computer-assisted intervention. Springer, 2015, pp. 234-241.
R. Zhao, B. Yaman, Y. Zhang, R. Stewart, A. Dixon, F. Knoll, Z. Huang, Y. W. Lui, M. S. Hansen, and M. P. Lungren, "fastmri+:

(56) References Cited

OTHER PUBLICATIONS

Clinical pathology annotations for knee and brain fully sampled multi-coil mri data," arXiv preprint arXiv:2109.03812, 2021.

* cited by examiner

PHYSICALLY-PRIMED DEEP-NEURAL-NETWORKS FOR GENERALIZED UNDERSAMPLED MRI RECONSTRUCTION

CROSS REFERENCE

This application claims priority from U.S. provisional patent Ser. No. 63/371,398 filing date Aug. 14, 2022 which is incorporated herein by reference.

BACKGROUND

There is a growing need to provide fast methods for generating high accuracy MRI images.

The following list includes some articles. This list does not indicate that any of the references is relevant.

[1] Z.-P. Liang and P. C. Lauterbur, Principles of magnetic resonance imaging. SPIE Optical Engineering Press Bellingham, 2000.

[2] J. Zbontar, F. Knoll, A. Sriram, T. Murrell, Z. Huang, M. J. Muckley, A. Defazio, R. Stern, P. Johnson, M. Bruno et al., "fastmri: An open dataset and benchmarks for accelerated mri," arXiv preprint arXiv:1811.08839, 2018.

[3] D. A. Feinberg, J. D. Hale, J. C. Watts, L. Kaufman, and A. Mark, "Halving mr imaging time by conjugation: demonstration at 3.5 kg." Radiology, vol. 161, no. 2, pp. 527-531, 1986.

[4] M. A. Griswold, P. M. Jakob, R. M. Heidemann, M. Nittka, V. Jellus, J. Wang, B. Kiefer, and A. Haase, "Generalized autocalibrating partially parallel acquisitions (grappa)," Magnetic Resonance in Medicine: An Official Journal of the International Society for Magnetic Resonance in Medicine, vol. 47, no. 6, pp. 1202-1210, 2002.

[5] K. P. Pruessmann, M. Weiger, M. B. Scheidegger, and P. Boesiger, "Sense: sensitivity encoding for fast mri," Magnetic Resonance in Medicine: An Official Journal of the International Society for Magnetic Resonance in Medicine, vol. 42, no. 5, pp. 952-962, 1999.

[6] K. Hammernik, T. Kustner, B. Yaman, Z. Huang, D. Rueckert, F. Knoll, and M. Akcakaya, "Physics-driven deep learning for computational magnetic resonance imaging," arXiv preprint arXiv:2203.12215, 2022.

[7] M. Lustig, D. Donoho, and J. M. Pauly, "Sparse mri: The application of compressed sensing for rapid mr imaging," Magnetic Resonance in Medicine: An Official Journal of the International Society for Magnetic Resonance in Medicine, vol. 58, no. 6, pp. 1182-1195, 2007.

[8] Y. Chen, C.-B. Schonlieb, P. Lio, T. Leiner, P. L. Dragotti, G. Wang, D. Rueckert, D. Firmin, and G. Yang, "Ai-based reconstruction for fast mri—a systematic review and meta-analysis," Proceedings of the IEEE, vol. 110, no. 2, pp. 224-245, 2022.

[9] T. Eo, Y. Jun, T. Kim, J. Jang, H.-J. Lee, and D. Hwang, "Kiki-net: cross-domain convolutional neural networks for reconstructing undersampled magnetic resonance images," Magnetic resonance in medicine, vol. 80, no. 5, pp. 2188-2201, 2018.

[10] A. Sriram, J. Zbontar, T. Murrell, A. Defazio, C. L. Zitnick, N. Yakubova, F. Knoll, and P. Johnson, "End-to-end variational networks for accelerated mri reconstruction," in International Conference on Medical Image Computing and Computer-Assisted Intervention. Springer, 2020, pp. 64-73.

[11] V. Antun, F. Renna, C. Poon, B. Adcock, and A. C. Hansen, "On instabilities of deep learning in image reconstruction and the potential costs of ai," Proceedings of the National Academy of Sciences, vol. 117, no. 48, pp. 30 088-30 095, 2020.

[12] A. Jalal, M. Arvinte, G. Daras, E. Price, A. G. Dimakis, and J. Tamir, "Robust compressed sensing mri with deep generative priors," Advances in Neural Information Processing Systems, vol. 34, pp. 14 938-14 954, 2021.

[13] F. Liu, A. Samsonov, L. Chen, R. Kijowski, and L. Feng, "Santis: sampling-augmented neural network with incoherent structure for mr image reconstruction," Magnetic resonance in medicine, vol. 82, no. 5, pp. 1890-1904, 2019.

[14] C. M. Hyun, H. P. Kim, S. M. Lee, S. Lee, and J. K. Seo, "Deep learning for undersampled mri reconstruction," Physics in Medicine & Biology, vol. 63, no. 13, p. 135007, 2018.

[15] G. Yang, S. Yu, H. Dong, G. Slabaugh, P. L. Dragotti, X. Ye, F. Liu, S. Arridge, J. Keegan, Y. Guo et al., "Dagan: deep de-aliasing generative adversarial networks for fast compressed sensing mri reconstruction," IEEE transactions on medical imaging, vol. 37, no. 6, pp. 1310-1321, 2017.

[16] S. Aja-Fernandez and G. Vegas-Sanchez-Ferrero, "Statistical analysis of noise in mri," Switzerland: Springer International Publishing, 2016.

[17] J. C. Ye, "Compressed sensing mri: a review from signal processing perspective," BMC Biomedical Engineering, vol. 1, no. 1, pp. 1-17, 2019.

[18] O. Ronneberger, P. Fischer, and T. Brox, "U-net: Convolutional networks for biomedical image segmentation," in International Conference on Medical image computing and computer-assisted intervention. Springer, 2015, pp. 234-241.

[19] R. Zhao, B. Yaman, Y. Zhang, R. Stewart, A. Dixon, F. Knoll, Z. Huang, Y. W. Lui, M. S. Hansen, and M. P. Lungren, "fastmri+: Clinical pathology annotations for knee and brain fully sampled multi-coil mri data," arXiv preprint arXiv:2109.03812, 2021.

SUMMARY

There may be provided systems, methods, and computer readable medium as illustrated in the specification.

BRIEF DESCRIPTION OF THE DRAWINGS

The embodiments of the disclosure will be understood and appreciated more fully from the following detailed description, taken in conjunction with the drawings in which the various figures illustrate examples of processes, systems, encoding, decoding and results.

DETAILED DESCRIPTION OF THE DRAWINGS

Figure 1:
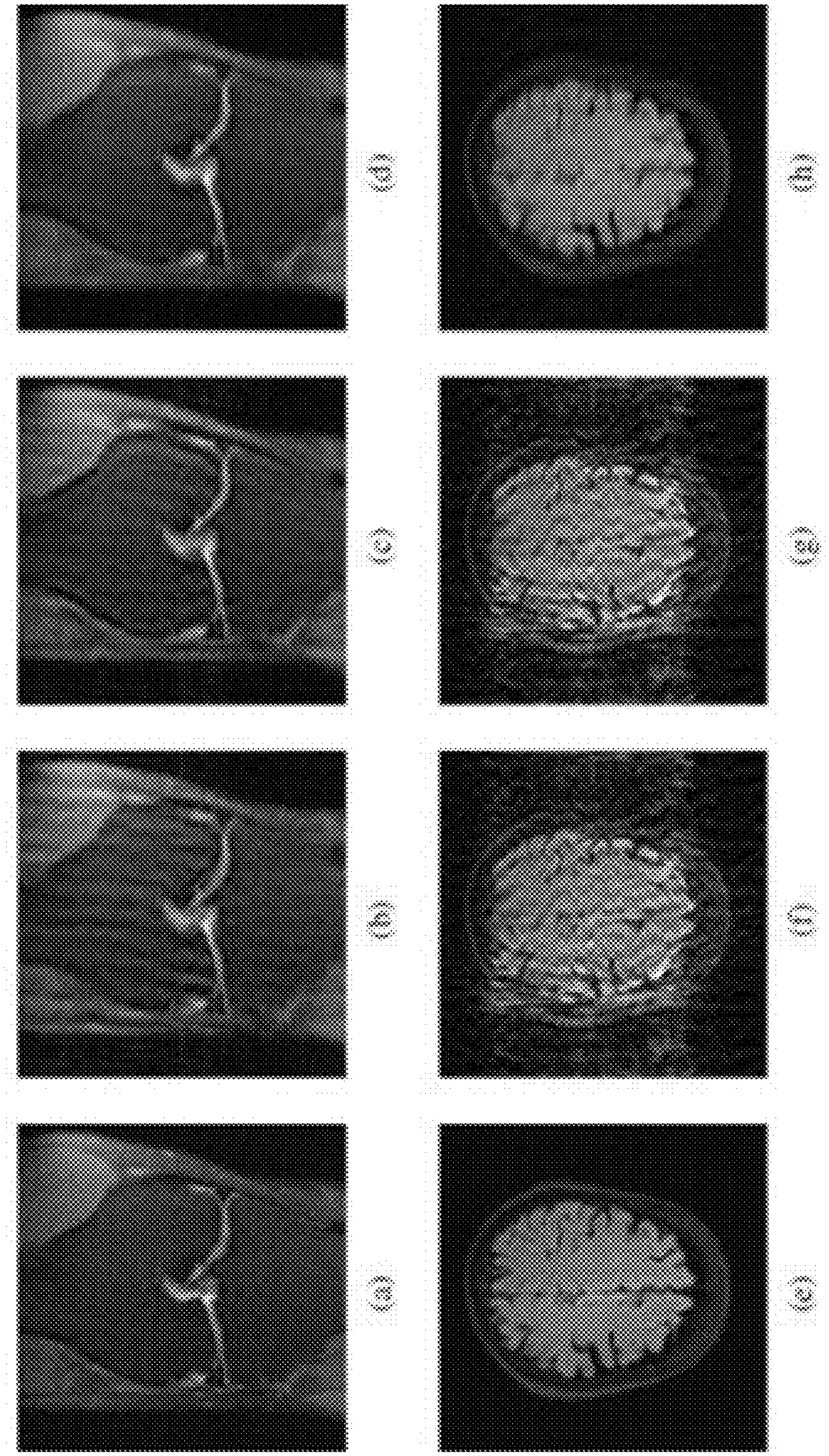
FIG. 1 illustrates the stability gap in DNN-based MRI reconstruction from undersampled data.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

Because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

Any reference in the specification to a method should be applied mutatis mutandis to a device or system capable of executing the method and/or to a non-transitory computer readable medium that stores instructions for executing the method.

Any reference in the specification to a system or device should be applied mutatis mutandis to a method that may be executed by the system, and/or may be applied mutatis mutandis to non-transitory computer readable medium that stores instructions executable by the system.

Any reference in the specification to a non-transitory computer readable medium should be applied mutatis mutandis to a device or system capable of executing instructions stored in the non-transitory computer readable medium and/or may be applied mutatis mutandis to a method for executing the instructions.

Any combination of any module or unit listed in any of the figures, any part of the specification and/or any claims may be provided.

The specification and/or drawings may refer to a processing circuit. The processing circuit may be implemented as a central processing unit (CPU), and/or one or more other integrated circuits such as application-specific integrated circuits (ASICs), field programmable gate arrays (FPGAs), full-custom integrated circuits, a graphics processing unit (GPU), a neural network processor, etc., or a combination of such integrated circuits.

Any combination of any steps of any method illustrated in the specification and/or drawings may be provided.

Any combination of any subject matter of any of claims may be provided.

Any combinations of systems, units, components, processors, sensors, illustrated in the specification and/or drawings may be provided.

Magnetic resonance imaging (MRI) is a non-invasive imaging modality with a wide range of clinical applications due to its capacity to provide detailed soft-tissue images. The MRI signal is acquired in the Fourier space, called the "k-space". An inverse Fourier transform (IFT) of the k-space is then applied to generate a meaningful MRI scan in the spatial domain [1]. Acquisition times required to sample the full k-space are a major limiting factor for achieving high spatial and temporal resolutions, reduce motion artifacts, improve patient experience and reduce costs [2].

Partial sampling of the k-space can linearly reduce acquisition times. However, the reconstruction of an MRI image from undersampled k-space data results in an highly ill-posed inverse problem. Naive reconstruction by zero-filling of the missing k-space data and application of the IFT results in a clinically meaningless image due to the presence of various artifacts [2]. Early works concentrated on the properties of the k-space, such as partial Fourier imaging methods that utilize Hermitian symmetry to reduce acquisition times [3].

Classical linear approaches for MRI reconstruction from undersampled data leverage advances in parallel imaging using multiple receiver coils coupled with linear algorithms for reconstruction applied either in the k-space domain [4] or in the spatial domain [5]. Nevertheless, the theoretical acceleration factor is bounded by the number of available coils [6]. The practical acceleration factor is further limited due to noise amplification resulted from the matrix inversion [5].

The non-linear compressed sensing (CS) [7] approach aims to reconstruct a high-quality image from undersampled k-space data by constraining the associated ill-posed inverse problem with a sparsity prior by means of a sparsifying linear transform. While the CS objective function does not have a closed form solution, it is a convex problem, and thus, can be solved using numerous iterative algorithms [6].

During the past few years, a plethora of deep-neural-networks (DNN) based methods were proposed for undersampled MRI reconstruction with substantial gains in both image quality and acceleration factors [8]. Similar to the classical methods, DNN-based methods can be applied in both the spatial domain and in the k-space domain. The KIKI-net, for example, alternates between the image domain (I-CNN) and k-space (K-CNN) iteratively, where a data consistency constraint is enforced in an interleaving manner [9]. The more recent End-to-End Variational Network (E2E-VarNet) simultaneously estimates coil-specific sensitivity maps and predicts the fully-sampled k-space from the undersampled k-space data through a series of cascades [10].

Despite the promising performance of currently available DNN methods, Antun et al. [11] and Jalal et al. [12] demonstrated that, unlike their classical counterparts, DNN-based methods are unstable against the presence of variations in the acquisition process and the anatomical distribution. Examples of such variations include using different undersampling mask or acceleration factor during inference compared to those used during training, and the presence of small pathologies or different anatomies compared to the data used for training.

Preliminary works aimed to address the stability gap in DNN-based MRI reconstruction through data augmentation techniques. Specifically, Liu et al. improves overall reconstruction performance and robustness against sampling pattern discrepancies and images acquired at different contrast phases by augmenting the undersampled data with extensively varying undersampling patterns [13]. More recently, Jalal et al. [12] combined DNN-based generative prior with classical CS-based reconstruction and posterior sampling to overcome the stability gap. However, this approach does not directly address the stability gap in DNN-based MRI reconstruction methods. More recently, physics-driven deep learning methods have emerged as a powerful tool to improve DNN-based undersampled MRI reconstruction generalization capacity. Spanning methods that incorporate physics of MRI acquisitions by means of physics-driven loss functions, plug-and-play methods, generative models, and unrolled networks [6]. Specific examples include enforcing k-space consistency directly after image enhancement [14], and adding k-space consistency as an additional cost function term during training [15].

Yet, the stability of DNN-based methods against variations in the acquisition process and the anatomical distribution remains an open question [6]. Further, current DNN methods formulate the ill-posed undersampled MRI reconstruction problem as a regression task, in which the goal is to predict the fully-sampled k-space data or high quality image from the undersampled data, effectively eliminating the sampling mask used during acquisition, from the regression process at inference time. This is in contrast to their classical counterparts which encode the sampling mask as part of the forward model of the system during the optimization process.

The suggested solution addresses the stability gap in undersampled MRI reconstruction with DNN by introducing a physically-primed DNN architecture and training approach. Unlike previous approaches, the suggested solution encodes the undersampling mask in addition to the observed data in the model architecture, and employs an appropriate training approach that uses data generated with various undersampling masks to encourage the model to generalize the undersampled MRI reconstruction problem.

The suggested solution introduces the physically-primed approach for DNN based MRI reconstruction from undersampled "k-space" data.

The suggested solution improves generalization capacity and robustness against variations in the acquisition process and the anatomical distribution.

The suggested solution was tested and experimental evidence for the improved robustness, especially in clinically relevant regions, using the publicly available fastMRI dataset is provided.

The suggested solution improves the generalization capacity of DNN methods for undersampled MRI reconstruction by introducing a physically-primed DNN architecture and training approach. The suggested solution architecture encodes the undersampling mask in addition to the observed data in the model architecture and employs an appropriate training approach that uses data generated with various undersampling masks to encourage the model to generalize the undersampled MRI reconstruction problem.

The suggested solution achieved an enhanced generalization capacity which resulted in significantly improved robustness against variations in the acquisition process and in the anatomical distribution, especially in pathological regions, compared to both vanilla DNN methods and DNN trained with undersampling mask augmentation. Trained models and code to replicate our experiments will become available for research purposes upon acceptance.

FIG. 1 illustrates the stability gap in DNN-based MRI reconstruction from undersampled data and includes two rows of images.

The first row includes images (a)-(d) that depicts variation in the acquisition process (different undersampling mask).

The second row includes images (e)-(h) presents variation in the anatomical distribution (train on knee data and inference on brain data).

Images (a) and (e) illustrate a target image from fully-sampled k-space data.

Images (b) and (f) illustrate a reconstruction using a model trained with a fixed sampling mask (Peak Signal To Noise Ratio (PSNR)=24.9/14.07, Structural Similarity index (SSIM)=0.4684/0.1926).

Images (c) and (g) illustrate a reconstruction using a model trained with mask augmentations (PSNR=25.35/16.56, SSIM=0.4969/0.2812).

Images (d) and (h) illustrate a reconstruction using the proposed physically-primed approach (PSNR=26.4/26.05, SSIM=0.5354/0.6359).

The forward model of the undersampled single coil MRI acquisition process is given by:

$$kus=M\circ\mathcal{F}x+n \tag{1}$$

Where kus$\in\mathbb{C}^N$ are the observed measurements in the k-space, x$\in\mathbb{R}^N$ is the image representing the underlying anatomy, F is the Fourier operator, M$\in$RN is a binary undersampling mask, $\circ$ is element-wise multiplication and n is an additive noise. For the sake of simplicity, we assume n~N(0, $\sigma^2$) [16].

Direct reconstruction of the MRI image x from the undersampled data is an ill-posed inverse problem that cannot simply solved using linear approaches. Naive reconstruction by zero-filling of the missing k-space data and application of the IFT will result in aliased image which is clinically meaningless [2].

The non-linear CS approach enables high-quality reconstruction from the undersampled k-space by imposing a sparsity constraint, $\psi$ to regularize the ill-posed inverse problem. The reconstructed image, $\hat{x}$, is obtained by solving the following constrained optimization problem:

$$\hat{x}=\underset{x}{\operatorname{argmin}}\|M\circ\mathcal{F}(x)-k_{us}\|_2+\lambda\psi(x) \tag{2}$$

Where $\lambda$ is the regularization weight balancing between the data term and the assumed prior. Examples to the sparsifying transform $\Psi$ include the total-variation and the wavelet transforms [7]. Recently, Jalal et al. [12] suggested to replace the sparsifying transform $\Psi$ with a DNN-based generative prior. Various optimization techniques were developed to address the challenging CS optimization problem [17]. Yet, the high computational complexity and limited ability to overcome image quality degradation at high acceleration rates may interfere clinical utilization [17].

Recently, DNN-based methods were applied for MRI reconstruction from undersampled data either on the image domain or on the k-space domain. In the k-space domain, the goal of these methods is to predict the fully sampled k-space data from the given undersampled k-space data. Without loss of generality, the prediction task can be represented as:

$$\widehat{k_{full}}=F_\theta(k_{us}) \tag{3}$$

Where $F_\theta$ denotes the network function and $\theta$ represents the DNN weights. Taking a supervised learning approach, the DNN weights $\theta$ are estimated by minimizing the loss between the full k-space data predicted by the DNN, $\widehat{k_{full}}$ from the undersampled data, kus, to the corresponding ground truth fully sampled k-space data, kfull, as follows:

$$\hat{\theta} = \underset{\theta}{\operatorname{argmin}} \sum_{i=0}^{n} \left\| F_\theta\left(k_{us}^{(i)}\right) - k_{full}^{(i)} \right\|_1 \quad (4)$$

However, unlike the classical CS approach (Eq. 2), such methods are known to be unstable against the presence of variations in the acquisition process and the anatomical distribution [11; 12].

A key observation is that while the CS approach (Eq. 2) explicitly encode the undersampling mask M as part of the system forward model, DNN-based approaches essentially ignore the undersampling mask during training an inference. Even though augmentation techniques suggest to use undersampled k-space data from different masks during training [13], or in a physically-motivated loss functions [6], yet the undersampling mask information is not explicitly encoded in the DNN architecture and leveraged during inference. This may result in DNN instability compared to the classical CS counterpart.

Methods

Physically-Primed DNN for MRI Reconstruction

The main hypothesis suggested by the inventors is that by explicitly encoding the undersampling mask in the DNN architecture and leveraging this information during inference, the DNN will be more capable to accurately generalize the ill-posed inverse problem associated with MRI reconstruction from undersampled data. Thus, it will be more robust against variations in the acquisition process and anatomical distribution.

There is provided a physically-primed, U-Net [18] based, DNN architecture operating on the k-space domain.

The complex-valued k-space data is represented as a two channel input, corresponding to the real and imaginary parts.

The encoding of the undersampling mask M included adding a $3^{rd}$ input channel to the DNN. The prediction of the full k-space data from the undersampled k-space data is defined as:

$$\widehat{k_{full}} = F_\theta(k_{us}, M) \quad (5)$$

The DNN weights θ are estimated by minimizing the loss between the full k-space data predicted by the DNN, $\widehat{k_{full}}$, from the undersampled data, kus and the undersampling mask M, to the corresponding ground truth fully sampled k-space data, kfull, as follows:

$$\hat{\theta} = \underset{\theta}{\operatorname{argmin}} \sum_{i=0}^{n} \left\| F_\theta\left(k_{us}^{(i)}, M^{(i)}\right) - k_{full}^{(i)} \right\|_1 \quad (6)$$

The physically-primed DNN model was encouraged to generalize the ill-posed inverse problem of MRI reconstruction from undersampled k-space data by varying the undersampling mask M during training.

Implementation Details

The used models are based on the suggested fastMRI U-Net [2], while modifying the output to be the summation of the k-space input and the network output. This network consists of two deep convolutional networks, an encoder followed by a decoder. The encoder consists of blocks of two 3×3 convolutions, each followed by Rectified Linear Unit (ReLU) activation functions. The input to the encoder is a 3-channel data representing the concatenation of the complex k-space data (2-channels) and the binary undersampling mask (1-channel). The output of each block is down-sampled using a max-pooling layer with stride 2.

The decoder consists of blocks with a similar structure to the encoder, where the output of each block is up-sampled using a bilinear up-sampling layer. The decoder concatenates the two inputs, the up-sampled output of the previous block and the output of the encoder block with the same resolution, to the first convolution in each block. At the end of the encoder there are two 1×1 convolutions that reduce the number of channels to two channels, representing the real and imaginary parts of the k-space data.

Figure 2:
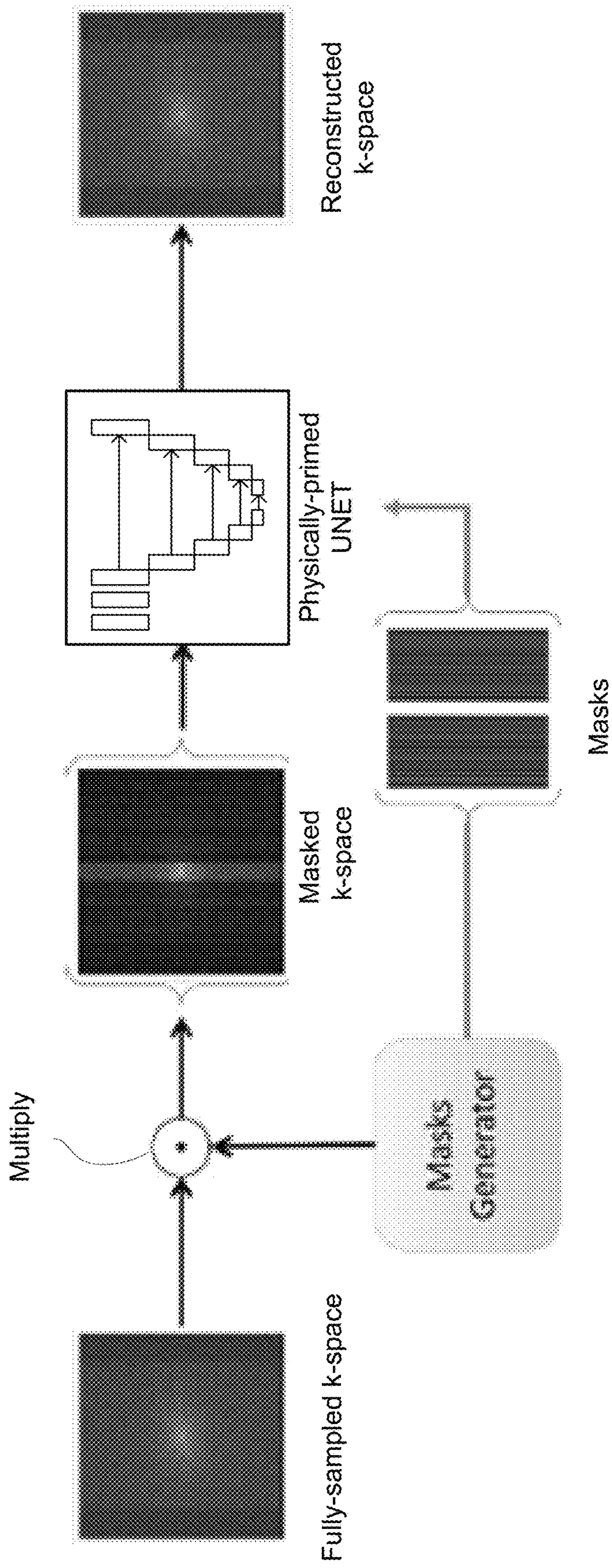
FIG. 2 illustrates an example of a physically-primed approach for training.

In the example illustrated in FIG. 2, the fully sampled k-space is multiplied by a binary mask to create the undersampled k-space. Then the undersampled k-space is fed into the physically primed DNN model along with the mask used for the sampling.

EXPERIMENTS

Dataset

The inventors used the publicly available fastMRI dataset [2], consisting of raw k-space data of knee and brain volumes. The knee images used in this study were directly obtained from the single coil track of the fastMRI dataset, while the brain images were reconstructed from fully sampled, multi-coil k-space data. Brain images were reconstructed by applying IFT to each individual coil and combining coils images with geometric averaging. The training set consisted of 34742 knee slices. The inventors split the fastMRI knee validation set into validation and test sets since the original fastMRI test set does not allow applying random undersampling. The splitting ratio was 2:1, yielding 5054 slices for validation and 2081 slices for test. Brain images (1000 slices) were used for test purposes only.

To further evaluate the clinical impact of our approach, the inventors also used the bounding box annotations generated by subspecialist experts on the fastMRI knee and brain dataset provided by the fastMRI+ dataset [19]. Each bounding box annotation includes its coordinates and the relevant label for a given pathology on a slice-by-slice level. Pathology annotations were marked in 39% of the training set, 28% of the validation set, and 51% of the test set. These annotations enabled us to examine the clinical relevance of our models performance on pathological regions.

Undersampling Masks

The inventors retrospectively undersampled the fully sampled k-space data by element-wise multiplication with randomly generated binary masks. The acceleration factor (R) was set to four or eight, where the undersampled k-space included 8% or 4% of the central region, respectively. The remaining k-space lines were sampled in three different ways to achieve the desired acceleration factor. The first sampling pattern was an equispaced mask with a fixed offset, meaning that the remaining k-space lines were sampled with equal spacing. The second sampling pattern was an equispaced mask with a varying offset, meaning that the remaining k-space lines were sampled with equal spacing but with random offset from the start. The third sampling pattern was a random mask, meaning that the remaining k-space lines were uniformly sampled.

Figure 3:
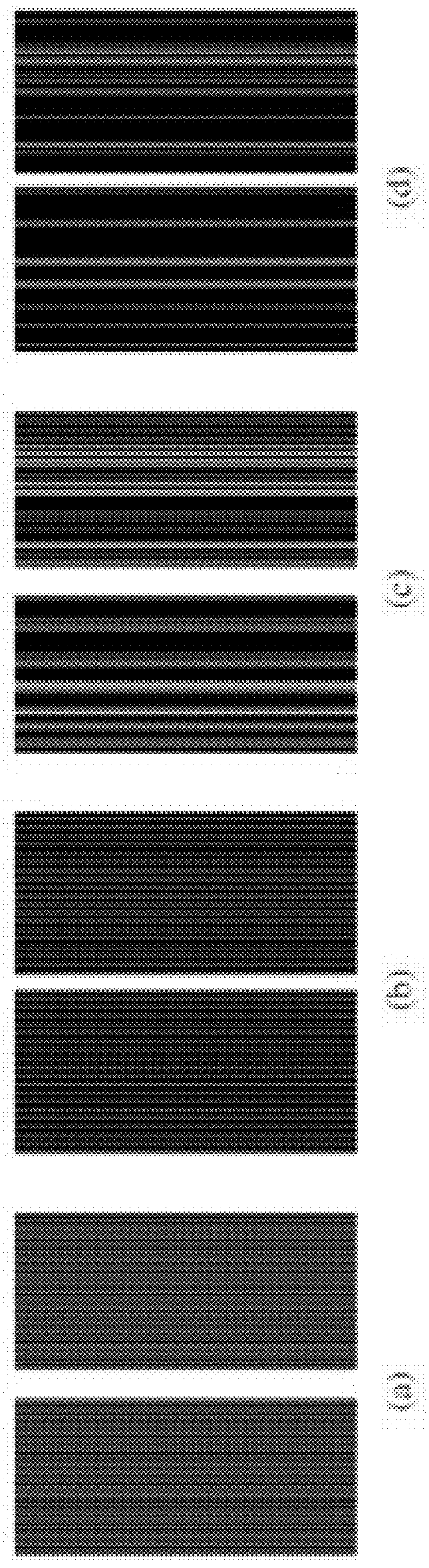
FIG. 3 depicts representative examples of four undersampling masks.

FIG. 3 depicts representative examples of four undersampling masks.

The first mask (denoted (a)) is an equispaced mask with R=4. The second mask (denoted (b)) is an equispaced mask with R=8. The third mask (denoted (c)) is a random mask with R=4. The fourth mask (denoted (d)) is a random mask with R=8.

Training Settings

The inventors trained three models on the undersampled k-space with R=4. The undersampling pattern of the first model was fixed equispaced (Fixed). The undersampling pattern of the two other models was varying equispaced, while the input of one of them is the two-channels k-space (Baseline), and the input of the second one consists of three channels where the third channel is the mask pattern (Mask). We trained the models on transformed k-space to account for the orders of magnitude difference between the DC coefficient and the rest of the coefficients in the k-space. Specifically we used the following transformation:

$$kt=\log(k+1)\cdot 10^5 \quad (7)$$

All models were trained using the RMSprop algorithm. The initial learning rates were optimized for each model. An initial learning rate of 0.01 was used for all models. The initial learning rate was multiplied by 0.1 after 40 epochs for all models. The inventors used the L1 norm between the 2 channels fully sampled k-space and the 2 channels reconstructed k-space as the loss function. The models were trained on two Nvidia A100 GPUs, each for 200 epochs. Training time took about 48 hours for each model. The inventors selected the models with the best validation loss for our experiments.

structed images along with zoom-in clinical annotation (bounding box) for variation in the acquisition process, i.e., knee data undersampled with a random mask and R=4 in test. Images (a) and (e) are target images. Images (b) and (f) illustrate a reconstruction of fixed model (PSNR=28.87/25.47, SSIM=0.6043/0.6524). Images (c) and (g) illustrate a reconstruction of baseline model (PSNR=29.12/25.98, SSIM=0.60122/0.663). Images (d) and (h) illustrate a reconstruction of mask model (PSNR=29.58/26.66, SSIM=0.6325/0.7026).

Figure 5:
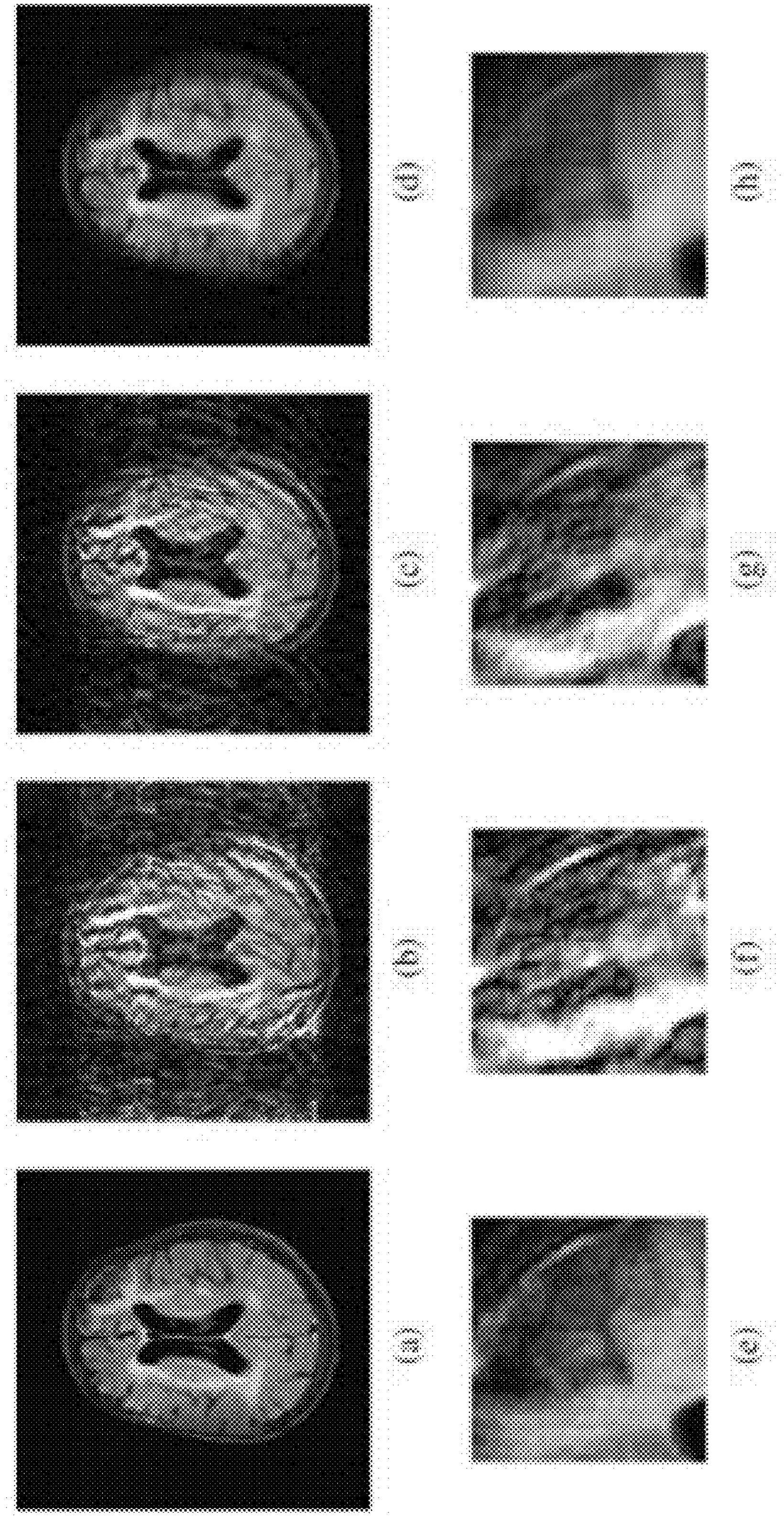
FIG. 5. presents representative reconstruction results in cases of variation in the anatomical distribution.

FIG. 5 presents representative reconstruction results in cases of variation in the anatomical distribution, i.e. brain images in test. Especially—FIG. 5 illustrates reconstructed images along with zoom-in clinical annotation (red bounding box) for variation in the anatomical distribution (brain data on test) undersampled with equispaced mask and R=4 in test.

Images (a) and (e) are target images. Images (b) and (f) illustrate a reconstruction of fixed model (PSNR=14.85) (10.92, SSIM=0.2405) (0.364). Images (c) and (g) illustrate a reconstruction of baseline model (PSNR=20.17) (15.53, SSIM=0.4315) (0.5377). Images (d) and (h) illustrate a reconstruction of mask model (PSNR=27.75) (24.67, SSIM=0.7446) (0.7779).

TABLE 1

Entire image reconstruction accuracy for varying equispaced mask patterns in test.

| R test | Model | NMSE | PSNR | SSIM |
|---|---|---|---|---|
| 4 | Fixed | 0.05064 +/− 0.05197 | 30.08 +/− 5.48 | 0.6783 +/− 0.217 |
| | Baseline | 0.04211 +/− 0.05201 | 31.18 +/− 6.422 | 0.704 +/− 0.2176 |
| | Mask | 0.04197 +/− 0.05204 | 31.2 +/− 6.438 | 0.7043 +/− 0.2177 |
| 8 | Fixed | 0.08887 +/− 0.06282 | 27.33 +/− 4.645 | 0.5604 +/− 0.262 |
| | Baseline | 0.08003 +/− 0.05827 | 27.8 +/− 4.706 | 0.5767 +/− 0.2476 |
| | Mask | 0.07905 +/− 0.05736 | 27.85 +/− 4.721 | 0.5805 +/− 0.2461 |

Experimental Methodology

The inventors examined the generalization capability of the networks by testing their performances with varying acquisition conditions and anatomical distributions. Specifically, the inventors evaluated reconstruction performance for: 1) undersampling patterns (equispaced for training and random for test) different from those used during training, but a similar acceleration factor (R=4), 2) different acceleration factor (R=4 for training and R=8 for test), and; 3) different anatomical distribution (knee for training and brain for test).

The inventors used standard evaluation metrics, including the average normalized mean square error (NMSE), Peak Signal-to-Noise Ratio (PSNR) and Structural Similarity (SSIM) to assess the different models performances. To specifically determine the clinical relevance of our approach, the inventors calculated performance metrics separately for the entire images and for clinically relevant regions that include pathologies. The inventors used the clinical regions annotations from the fastMRI+ dataset [19]. The inventors determined statistically significant differences between our approach and a baseline model trained with undersampling mask data augmentation with a paired Student's t-test.

Results

Figure 4:
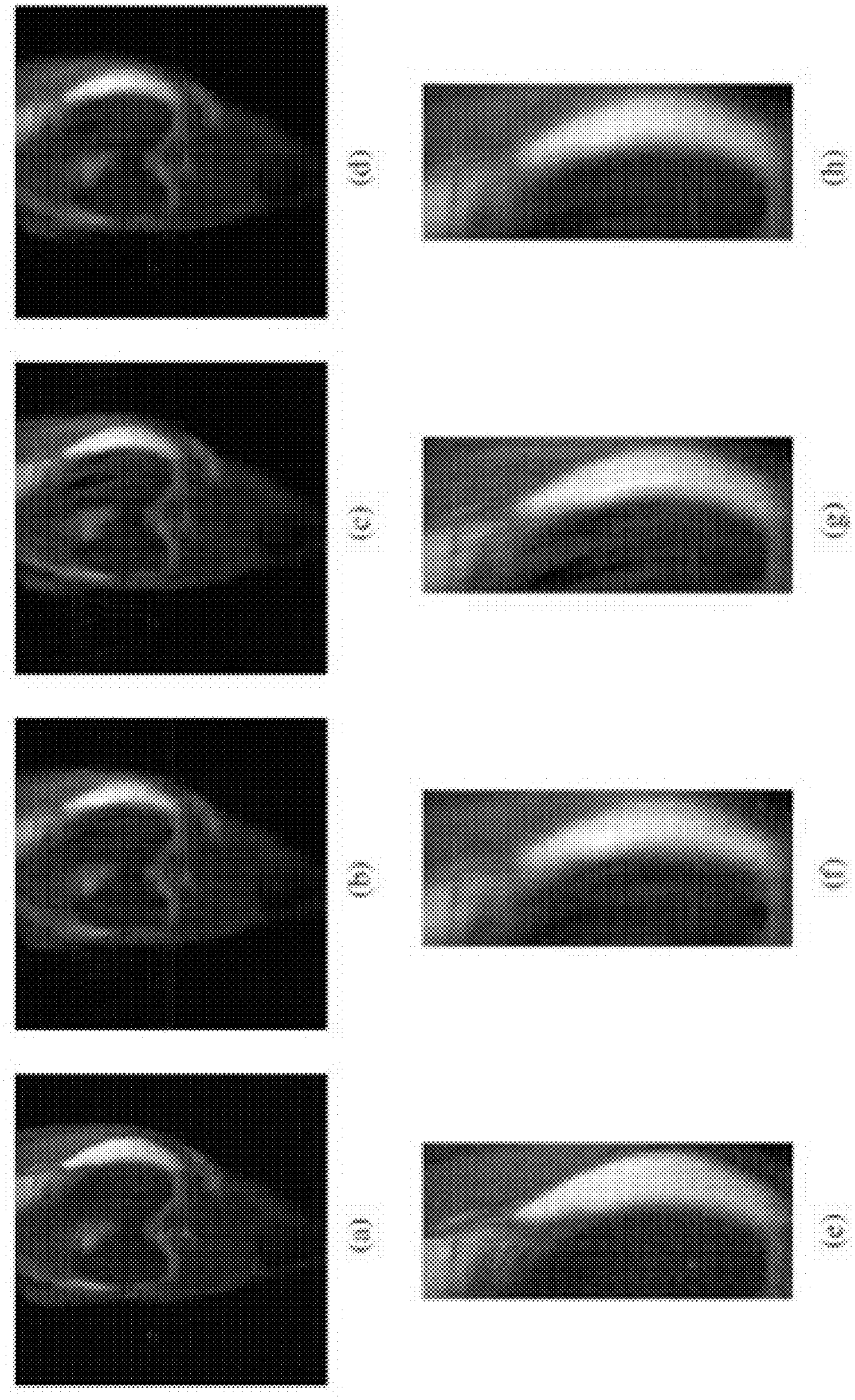
FIG. 4 presents representative reconstruction results in cases of similar anatomical distribution and variation in the acquisition process.

FIG. 4 presents representative reconstruction results in cases of similar anatomical distribution and variation in the acquisition process, i.e. knee images with R=4 and different sampling masks in test. Especially—FIG. 4 illustrates recon- Tables 1 and 2 summarize model performance on the entire image and for the clinically relevant regions, respectively, for the same anatomical distribution (i.e knee data) but with variations in the acquisition process (i.e. different equispaced sampling mask). Similarly, Tables 3 and 4 summarize model performance for random sampling masks in test. In all cases, the physically-primed model (Mask) has significantly better reconstruction accuracy (Paired student's t-test, $p \ll 0.01$). The improved accuracy indicates a better generalization and robustness against variations in the acquisition process compared to models trained with and without mask augmentation. It is important to note that the improved performance is evident mostly in the clinically-relevant regions which are critical for clinical diagnosis.

Tables 5 and 6 demonstrate the generalization capacity of the suggested physically-primed model in case of variation in the anatomical distribution, i.e. training on knee data while testing on brain data for the entire image and for the clinically-relevant regions, respectively. The suggested physically-primed model (mask) performed significantly better (Paired student's t-test, $p \ll 0.01$) than the models trained with and without mask augmentation.

The improved robustness of the suggested physically-primed model against variations in both the acquisition process and the anatomical distribution, suggest better generalization capacity beyond more common data augmentation techniques.

TABLE 2

Pathological regions reconstruction accuracy for varying equispaced mask patterns in test.

| R test | Model | NMSE | PSNR | SSIM |
|---|---|---|---|---|
| 4 | Fixed | 0.06059 +/− 0.09013 | 20.36 +/− 5.133 | 0.6374 +/− 0.266 |
| | Baseline | 0.05073 +/− 0.07628 | 21.22 +/− 5.332 | 0.6797 +/− 0.2415 |
| | Mask | 0.05013 +/− 0.07356 | 21.26 +/− 5.327 | 0.6807 +/− 0.2408 |
| 8 | Fixed | 0.1324 +/− 0.3375 | 17.07 +/− 4.649 | 0.4268 +/− 0.3105 |
| | Baseline | 0.1223 +/− 0.2854 | 17.44 +/− 4.755 | 0.4528 +/− 0.3083 |
| | Mask | 0.1193 +/− 0.3246 | 17.59 +/− 4.659 | 0.4638 +/− 0.3014 |

TABLE 3

Entire image reconstruction accuracy for random mask in test.

| R test | Model | NMSE | PSNR | SSIM |
|---|---|---|---|---|
| 4 | Fixed | 0.05759 +/− 0.05625 | 29.47 +/− 5.453 | 0.6374 +/− 0.2411 |
| | Baseline | 0.05187 +/− 0.05623 | 30.08 +/− 5.931 | 0.6519 +/− 0.239 |
| | Mask | 0.05013 +/− 0.05547 | 30.23 +/− 5.955 | 0.6592 +/− 0.2357 |
| 8 | Fixed | 0.09473 +/− 0.06802 | 27.07 +/− 4.672 | 0.5403 +/− 0.2815 |
| | Baseline | 0.08718 +/− 0.06259 | 27.42 +/− 4.636 | 0.552 +/− 0.2674 |
| | Mask | 0.08557 +/− 0.06079 | 27.49 +/− 4.665 | 0.5549 +/− 0.2597 |

TABLE 4

Pathological regions reconstruction accuracy for random mask in test.

| R test | Model | NMSE | PSNR | SSIM |
|---|---|---|---|---|
| 4 | Fixed | 0.07082 +/− 0.1018 | 19.62 +/− 4.839 | 0.5815 +/− 0.2899 |
| | Baseline | 0.06401 +/− 0.09236 | 20.12 +/− 5.008 | 0.6091 +/− 0.281 |
| | Mask | 0.05946 +/− 0.0852 | 20.43 +/− 4.973 | 0.6206 +/− 0.2713 |
| 8 | Fixed | 0.1377 +/− 0.2631 | 16.77 +/− 4.577 | 0.391 +/− 0.3098 |
| | Baseline | 0.1311 +/− 0.2524 | 17.06 +/− 4.713 | 0.4096 +/− 0.3123 |
| | Mask | 0.1228 +/− 0.2367 | 17.31 +/− 4.644 | 0.429 +/− 0.3048 |

TABLE 5

Entire image reconstruction accuracy on brain dataset for fixed equispaced mask in test.

| R test | Model | NMSE | PSNR | SSIM |
|---|---|---|---|---|
| 4 | Fixed | 0.182 +/− 0.3004 | 22.23 +/− 7.154 | 0.5093 +/− 0.2493 |
| | Baseline | 0.1147 +/− 0.1303 | 23.35 +/− 5.51 | 0.5455 +/− 0.1786 |
| | Mask | 0.02199 +/− 0.01034 | 29.92 +/− 4.55 | 0.7442 +/− 0.139 |
| 8 | Fixed | 0.1312 +/− 0.1226 | 22.48 +/− 5.041 | 0.412 +/− 0.2257 |
| | Baseline | 0.1053 +/− 0.129 | 23.53 +/− 4.57 | 0.4587 +/− 0.2068 |
| | Mask | 0.04726 +/− 0.0242 | 26.64 +/− 4.189 | 0.6628 +/− 0.1576 |

TABLE 6

Pathological regions reconstruction accuracy on brain dataset for fixed equispaced mask in

| R test | Model | NMSE | PSNR | SSIM |
|---|---|---|---|---|
| 4 | Fixed | 0.1542 +/− 0.7087 | 16.41 +/− 8.643 | 0.3731 +/− 0.4088 |
| | Baseline | 0.105 +/− 0.3544 | 17.65 +/− 7.585 | 0.4185 +/− 0.4031 |
| | Mask | 0.02502 +/− 0.06294 | 23.8 +/− 7.615 | 0.6421 +/− 0.2506 |
| 8 | Fixed | 0.105 +/− 0.235 | 16.87 +/− 6.588 | 0.294 +/− 0.356 |
| | Baseline | 0.09502 +/− 0.2554 | 17.68 +/− 7.031 | 0.3007 +/− 0.3833 |
| | Mask | 0.04952 +/− 0.1054 | 20.78 +/− 7.396 | 0.4544 +/− 0.2891 |

DISCUSSION AND CONCLUSION

The inventors introduced a physically-primed DNN architecture to address the stability gap in deep-learning based MRI reconstruction from undersampled k-space data. The previously observed stability gap indicates limited generalization of the associated ill-posed inverse problem compared to classical methods. This stability gap practically impede DNN-based MRI reconstruction from undersampled data in the clinical setting. While previous approaches aimed to address the stability gap through data augmentation and physically motivated loss functions, the suggested physically-primed DNN approach improves the generalization capacity by encoding the forward model, including the undersampling mask, in the network architecture and introducing an appropriate training scheme with samples generated with various undersampling masks. The experiments showed that encoding the undersampling mask as part of the DNN architecture improves generalization capacity, especially in clinically relevant regions, compared to previously proposed data augmentation techniques in multiple scenarios including changing the undersampling mask, modifying the sampling factor, and applying the DNN to reconstruct images acquired from a different anatomical region.

It should be noted that the encoding of the undersampling mask into the DNN architecture can be executed in manners that differ from the illustrated encoding scheme.

It should be noted that the outcome of the method can be evaluated by using quantitative metrics other than PSNR and SSIM.

In conclusion, physically-primed approach has the potential to improve the generalization capacity and robustness of DNN-based methods for MRI reconstruction from undersampled k-space data. Thus, in turn, the inventors approach has the potential to facilitate the utilization of DNN-based MRI reconstruction methods in the clinical setting.

Figure 6:
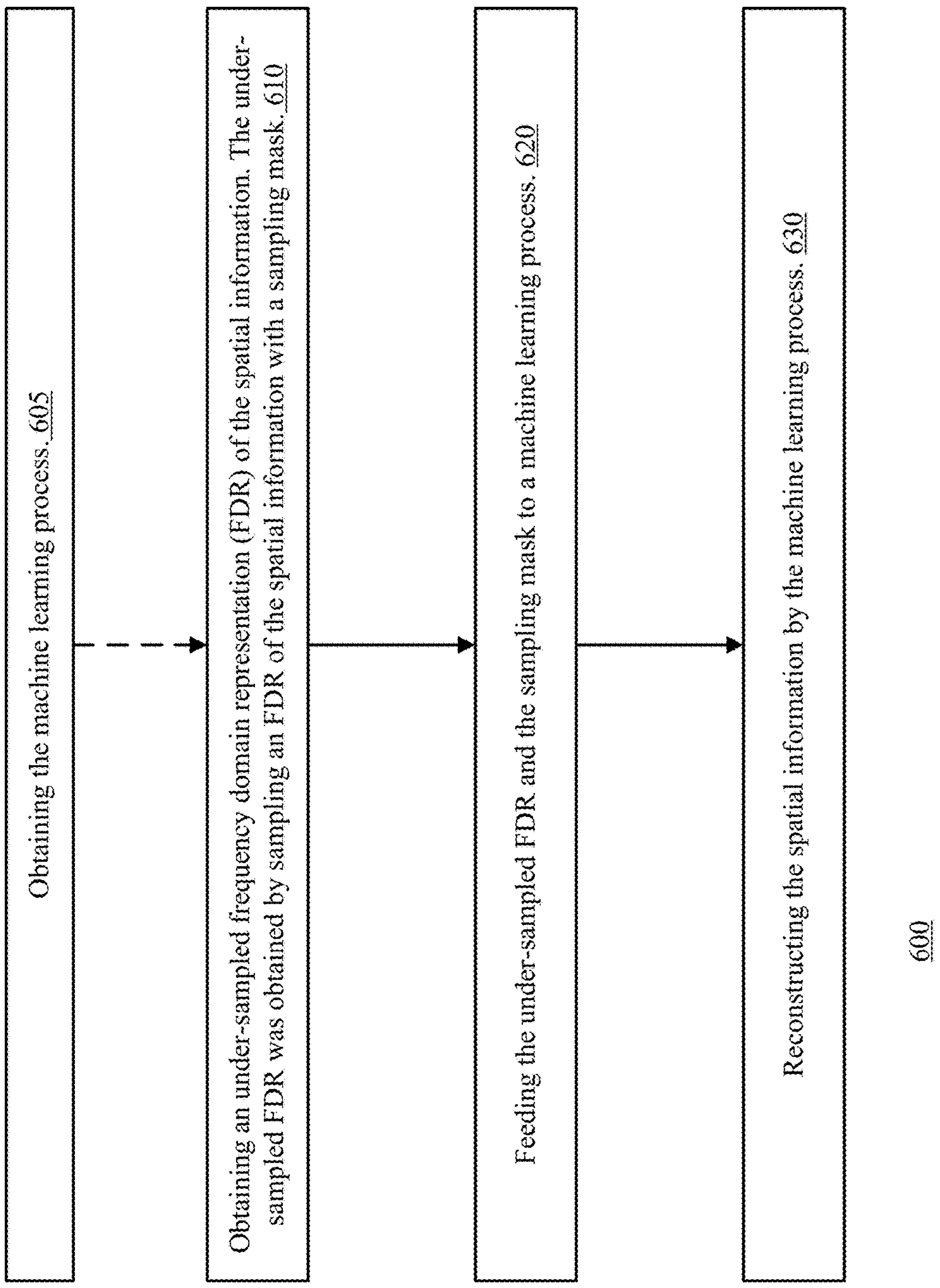
FIG. 6. presents an example of a method.

FIG. 6 illustrates an example of a method 600 for reconstructing spatial information.

According to an embodiment, method 600 includes step 610 of obtaining an under-sampled frequency domain representation (FDR) of the spatial information. The under-sampled FDR was obtained by sampling an FDR of the spatial information with a sampling mask.

According to an embodiment, the FDR of the spatial information is a Fourier transform representation of the spatial information. The FDR may be generated by means other than applying a Fourier transform.

According to an embodiment step 610 includes at least one of:

- Receiving the under-sampled FDR of the spatial information.
- Receiving the sampling mask.
- Generating the under-sampled FDR of the spatial information.
- Generating the sampling mask.
- Receiving the spatial information and generating the under-sampled FDR of the spatial information, using the sampling mask.
- Generating the spatial information and generating the under-sampled FDR of the spatial information, using the sampling mask.
- Generating the spatial information by an magnetic resonance imaging (MRI) system.
- Generating the spatial information by a single coil of the MRI system.
- Generating the spatial information by multiple coils of the MRI system.
- Generating the spatial information that differs from MRI spatial information.
- Controlling a generation of the spatial information.
- Controlling a generation of the spatial information by one or more coils of an magnetic resonance imaging (MRI) system.

According to an embodiment, step 610 is followed by step 620 of feeding the under-sampled FDR and the sampling mask to a machine learning process.

The machine learning process may be one or more neural networks or may differ from one or more neural networks.

According to an embodiment the one or more neural networks include any type of neural network—for example:

- A UNET neural network and/or
- A transformer neural network.
- An end-to-end variational network.
- A sampling mask encoder and an under-sampled FDR encoder.

According to an embodiment the machine learning process are implemented by one or more processing circuits.

According to an embodiment the one or more integrated circuits belong to the source of the spatial information—for example may belong to an MRI system.

According to an embodiment the one or more integrated circuits are in communication with the source of the spatial information—for example may be in communication with the MRI system—for example over one or more networks of any type, may belong to a remote computer or to a computer that is proximate to the source of the spatial information.

According to an embodiment, step 620 is followed by step 630 of reconstructing the spatial information by the machine learning process.

According to an embodiment, method 600 includes step 605 of obtaining the machine learning process.

Step 605 may include at least one of:

- Receiving the machine learning process—after the machine learning process was trained.
- Training the machine learning process using a training data set.
- Testing the machine learning process using a test data set.

The machine learning process was trained using a training data set that may include training undersampled FDRs of training spatial information, and one or more training sampling masks that were used to sample FDRs of training spatial information. The one or more training sampling masks may be multiple training sampling masks, and wherein at least two of the training sampling masks differ from each other.

According to an embodiment, at least one training sampling mask of the one or more training sampling masks differs from the sampling mask. Thus—the sampling mask applied during inference differs from the training sample masks.

According to an embodiment, The training spatial information includes multiple training spatial information units, wherein at least one of the training spatial information units may be related to an object that differs from an object related to the spatial information. Thus—the training may be done with images of a certain object while the inference can be done in relation to another object.

Figure 7:
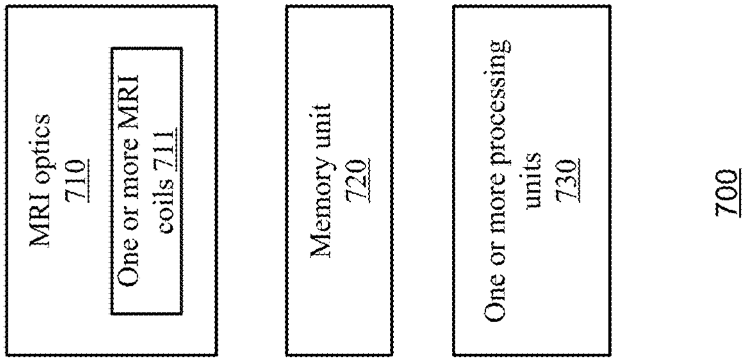
FIG. 7 illustrates an example of an MRI system.

FIG. 7 illustrates a system 700 for reconstructing spatial information. In FIG. 7 the system 700 is an MRI system that includes optics 710 (including one or more coils 711) for generating spatial information such as a MRI information, memory unit 720 for storing the spatial information and/or for storing instructions for controlling the operation of the optics and/or for controlling the execution of method 600, and one or more processing circuits 730 that are configured to (for example programmed to) generate an FDR of the spatial information using a sampling mask, and host a machine learning process that reconstructs the spatial information. The one or more processing circuits may use a single sampling mask or may select between multiple sampling masks.

According to an embodiment, at least one processing circuit does not belong to the MRI system (may belong to a computerized system that is in communication with the MRI system) and may receive the FDR of the spatial information, and hosts a machine learning process that reconstructs the spatial information. According to an embodiment the FDR of the MRI information is determined using at least one processing circuit that does not belong to the MRI system.

There is provided a non-transitory computer readable medium for reconstructing spatial information, the non-transitory computer readable medium stores instructions for: obtaining an frequency domain representation (FDR) of the spatial information, wherein the under sampled under-sampled FDR was obtained by sampling an FDR of the spatial information with a sampling mask; feeding the FDR and the sampling mask to a machine learning process; and reconstructing the spatial information by the machine learning process. The machine learning process was trained using a training data set that comprises training undersampled FDRs of training spatial information, and one or more training sampling masks that were used to sample FDRs of training spatial information.

According to an embodiment, the one or more training sampling masks are multiple training sampling masks, and wherein at least two of the training sampling masks differ from each other.

According to an embodiment, the FDR of the spatial information is magnetic resonance imaging (MRI) information.

According to an embodiment, the MRI information is obtained from a single coil of an MRI system.

According to an embodiment, the MRI information is obtained from multiple coils of an MRI system.

According to an embodiment, the FDR of the spatial information is a Fourier transform representation of the spatial information.

According to an embodiment, the machine learning process is implemented by one or more neural networks.

According to an embodiment, the one or more neural networks comprise a UNET.

According to an embodiment, the one or more neural networks comprise a transformer neural network.

According to an embodiment, the one or more neural networks comprise an end-to-end variational network.

According to an embodiment, the one or more neural networks comprise a sampling mask encoder and an under-sampled FDR encoder.

According to an embodiment, the at least one training sampling mask of the one or more training sampling masks differs from the sampling mask.

According to an embodiment, the training spatial information comprises multiple training spatial information units, wherein at least one of the training spatial information units is related to an object that differs from an object related to the spatial information.

According to an embodiment, the non-transitory computer readable medium stores instructions for training the machine learning process using the training data set.

According to an embodiment, the non-transitory computer readable medium stores instructions for testing the machine learning process using a test data set.

According to an embodiment, the non-transitory computer readable medium stores instructions for controlling a generation of the spatial information.

According to an embodiment, the non-transitory computer readable medium stores instructions for controlling a generation of the spatial information by one or more coils of an magnetic resonance imaging (MRI) system.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

In the foregoing specification, the invention has been described with reference to specific examples of embodiments of the invention. It will, however, be evident that various modifications and changes may be made therein without departing from the broader spirit and scope of the invention as set forth in the appended claims.

Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures may be implemented which achieve the same functionality.

Any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated can also be viewed as being "operably connected," or "operably coupled," to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

Also for example, in one embodiment, the illustrated examples may be implemented as circuitry located on a single integrated circuit or within a same device. Alternatively, the examples may be implemented as any number of separate integrated circuits or separate devices interconnected with each other in a suitable manner.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

It is appreciated that various features of the embodiments of the disclosure which are, for clarity, described in the contexts of separate embodiments may also be provided in combination in a single embodiment. Conversely, various features of the embodiments of the disclosure which are, for brevity, described in the context of a single embodiment may also be provided separately or in any suitable sub-combination.

It will be appreciated by persons skilled in the art that the embodiments of the disclosure are not limited by what has been particularly shown and described hereinabove. Rather the scope of the embodiments of the disclosure is defined by the appended claims and equivalents thereof.

We claim:

1. A method for reconstructing spatial information, the method comprises:

obtaining an frequency domain representation (FDR) of the spatial information, wherein the under-sampled FDR was obtained by sampling an FDR of the spatial information with a sampling mask;

feeding the under-sampled FDR and the sampling mask to a machine learning process; and reconstructing the spatial information by the machine learning process;

wherein the machine learning process was trained using a training data set that comprises training undersampled FDRs of training spatial information, and one or more training sampling masks that were used to sample FDRs of training spatial information.

2. The method according to claim 1 wherein the one or more training sampling masks are multiple training sampling masks, and wherein at least two of the training sampling masks differ from each other.

3. The method according to claim 1 wherein the FDR of the spatial information is magnetic resonance imaging (MRI) information.

4. The method according to claim 3 wherein the MRI information is obtained from a single coil of an MRI system.

5. The method according to claim 3 wherein the MRI information is obtained from multiple coils of an MRI system.

6. The method according to claim 1 wherein the FDR of the spatial information is a Fourier transform representation of the spatial information.

7. The method according to claim 1 wherein the machine learning process is implemented by one or more neural networks.

8. The method according to claim 7 wherein the one or more neural networks comprise a UNET.

9. The method according to claim 7 wherein the one or more neural networks comprise a transformer neural network.

10. The method according to claim 7 wherein the one or more neural networks comprise an end-to-end variational network.

11. The method according to claim 7 wherein the one or more neural networks comprise a sampling mask encoder and an under-sampled FDR encoder.

12. The method according to claim 1 wherein at least one training sampling mask of the one or more training sampling masks differs from the sampling mask.

13. The method according to claim 1 wherein the training spatial information comprises multiple training spatial information units, wherein at least one of the training spatial information units is related to an object that differs from an object related to the spatial information.

14. The method according to claim 1 wherein the machine learning process is implemented by one or more neural networks that comprises a deep neural network, wherein the sampling mask is explicitly encoded in the deep neural network.

15. The method according to claim 14, wherein the deep neural network comprises an input channel that is dedicated to receive the sampling mask.

16. A non-transitory computer readable medium for reconstructing spatial information, the non-transitory computer readable medium stores instructions for:

obtaining an frequency domain representation (FDR) of the spatial information, wherein the under-sampled FDR was obtained by sampling an FDR of the spatial information with a sampling mask;

feeding the under-sampled FDR and the sampling mask to a machine learning process; and reconstructing the spatial information by the machine learning process;

wherein the machine learning process was trained using a training data set that comprises training undersampled FDRs of training spatial information, and one or more training sampling masks that were used to sample FDRs of training spatial information.

17. The non-transitory computer readable medium according to claim 16 that stores instructions for controlling a generation of the spatial information.

18. The non-transitory computer readable medium according to claim 16 that stores instructions for controlling a generation of the spatial information by one or more coils of an magnetic resonance imaging (MRI) system.

19. A computerized system comprises a processor that is configured to:

obtain an frequency domain representation (FDR) of the spatial information, wherein the under-sampled FDR was obtained by sampling an FDR of the spatial information with a sampling mask;

implement a machine learning process that once fed with the under-sampled FDR and the sampling mask, reconstructs the spatial information;

wherein the machine learning process was trained using a training data set that comprises training undersampled FDRs of training spatial information, and one or more training sampling masks that were used to sample FDRs of training spatial information.

20. The computerized system according to claim 19 wherein the computerized system is an MRI system.

* * * * *